US012806605B2

(12) United States Patent
Allaire et al.

(10) Patent No.: US 12,806,605 B2
(45) Date of Patent: Nov. 24, 2026

(54) CATALYST STACKED BED SYSTEM WITH VARYING METAL CONCENTRATION FOR TRANSALKYLATION PROCESS

(71) Applicant: UOP LLC, Des Plaines, IL (US)

(72) Inventors: Kristen E. Allaire, Chicago, IL (US); Rajesh Rajappan, Buffalo Grove, IL (US); Raymond Shih, Kildeer, IL (US); Laxmikant Bharuka, Haryana (IN)

(73) Assignee: UOP LLC, Des Plaines, IL (US)

( * ) Notice: Subject to any disclaimer, the term of this patent is extended or adjusted under 35 U.S.C. 154(b) by 550 days.

(21) Appl. No.: 18/465,302

(22) Filed: Sep. 12, 2023

(65) Prior Publication Data

US 2025/0083135 A1 Mar. 13, 2025

(51) Int. Cl.
*B01J 29/076* (2006.01)
*B01J 23/28* (2006.01)
*C07C 6/12* (2006.01)

(52) U.S. Cl.
CPC ............. *B01J 29/076* (2013.01); *B01J 23/28* (2013.01); *C07C 6/126* (2013.01)

(58) Field of Classification Search
None
See application file for complete search history.

(56) References Cited

U.S. PATENT DOCUMENTS 7,385,098 B2 6/2008 Nanda
7,419,931 B2 9/2008 Serra et al.
7,597,795 B2 10/2009 Schleicher et al.
7,626,064 B1 12/2009 Boldingh et al.
7,897,825 B2 3/2011 Levin
7,947,621 B2 5/2011 Chang et al.
8,481,443 B2 * 7/2013 Levin ........................ C07C 6/12 502/67
10,010,878 B2 7/2018 Moscoso et al.
10,647,633 B2 5/2020 Soultanidis et al.
10,781,149 B2 * 9/2020 Molinier ................. C07C 6/126
2002/0082460 A1 6/2002 Verduijn et al.
2006/0100471 A1 5/2006 Serra Alfaro et al.
2007/0055086 A1 3/2007 Buchanan et al.
2010/0093520 A1 4/2010 Levin
2013/0225891 A1 8/2013 Ross et al.
2013/0259775 A1 10/2013 Levin et al.
2019/0232262 A1 8/2019 Li et al.
2020/0031737 A1 1/2020 Elias et al.
2021/0129122 A1 5/2021 Lee et al.
2022/0266224 A1 8/2022 Dong et al.

FOREIGN PATENT DOCUMENTS

CN 1721069 A 1/2006
CN 112661590 A 4/2021
CN 115518680 A 12/2022
CN 115532306 A 12/2022
KR 20180112072 A 10/2018
WO 2021216176 A1 10/2021
WO 2022063266 A1 3/2022

OTHER PUBLICATIONS

International Search Report from corresponding PCT application No. PCT/US2024/045344 dated Dec. 16, 2024.
Written Opinion from corresponding PCT application No. PCT/US2024/045344 dated Dec. 16, 2024.
Robert W. Broach et al., Tailoring zeolite morphology by Charge Density Mismatch for aromatics processing, Journal of Catalysis 308 (2013) 143-153.

* cited by examiner

*Primary Examiner* — Stefanie J Cohen

(57) ABSTRACT

A catalyst stacked bed system with varying metal concentration for transalkylation and a method of transalkylation utilizing the catalyst are described. There is a first catalyst bed comprising a zeolite and a metal on top of a second catalyst bed comprising the same zeolite and metal in order to optimize performance benefits. The catalyst stacked bed system may comprise two or more catalyst beds. The first catalyst bed is positioned to contact the feed before the second (or subsequent) catalyst bed. The first catalyst bed has a total metal content of 1 wt % or more, and its total metal content is higher than the second catalyst bed. Each subsequent bed has a lower metal content than the previous bed. The metal for the first and second bed is selected from Groups 6-10 and 14 of the Periodic Table, or combinations thereof.

19 Claims, No Drawings

CATALYST STACKED BED SYSTEM WITH VARYING METAL CONCENTRATION FOR TRANSALKYLATION PROCESS

BACKGROUND

Transalkylation is a chemical reaction resulting in transfer of an alkyl group from one organic compound to another. Transalkylation is used in the refining industry to convert a feed comprising mainly of $C_6$-$C_{11}$ aromatic molecules into aromatic products, particularly benzene, toluene and xylene (BTX). Catalysts, particularly zeolite catalysts, are often used to produce the reaction. If desired, the transalkylation catalyst may be metal stabilized using a noble metal or base metal and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream comprising unconverted feed and product monoalkylated hydrocarbons. This effluent is normally cooled and passed to a stripping column in which substantially all C5 and lighter hydrocarbons present in the effluent are concentrated into an overhead stream and removed from the process. An aromatics-rich stream is recovered as net stripper bottoms, which is referred to as the transalkylation effluent.

The transalkylation reaction can be produced in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The catalyst is typically selected to have relatively high stability at a high activity level.

One difficulty that may arise in the transalkylation process relates to the action of the catalyst. To an extent, increasing the metal concentration of the catalyst improves stability and xylene selectivity, but the benzene purity of the transalkylated product stream may be too low for some aromatics producers, thus compromising the purity of their final benzene product. For example, the benzene product after transalkylation and subsequent fractionation must exceed 99.3% purity in order to be sold commercially. Increasing catalyst metal content increases xylene yield by increasing the dealkylation activity of $C_{9+}$ aromatics, but it also increases hydrogenation leading to increased conversion to benzene coboiler molecules, which are typically paraffinic and naphthenic molecules with 6 or 7 carbon atoms. The benzene purity of the transalkylated product can be improved by lowering the metal content in the catalyst, but the xylene selectivity is not as high as with catalysts having higher metal content. If required, aromatics producers may also improve the benzene purity of their transalkylation product by an extraction step; however, this increases the cost of production.

Therefore, there is a need for a transalkylation catalyst system that provides both high xylene selectivity and high benzene purity.

DETAILED DESCRIPTION

The present invention meets this need by providing a solution with high xylene selectivity, low ring loss, high benzene purity, and long catalyst life. The system stacks a first catalyst bed comprising at least one zeolite and a metal on top of a second catalyst bed comprising the same zeolite formulation and metal as the first catalyst bed in order to optimize performance benefits. The first catalyst bed is positioned to contact the feed before the second (or subsequent) catalyst bed. The first catalyst bed has a total metal content of 1 wt % or more, and its total metal is higher than any other bed.

It has been demonstrated that stacking a catalyst with a higher metal content catalyst on top of a catalyst with a lower metal content in a downflow transalkylation process provides a solution with a xylene selectivity as good as the catalyst with the higher metal content and a benzene purity comparable to a catalyst with a lower metal content. Although not intended to be bound by theory, it is hypothesized that by stacking the catalyst with the higher total metal content on top (the first to contact the feed), increased xylene is produced and maintained in the bottom bed (lower or following beds) with the lower total metal content. Having the catalyst with the lower metal content in the bottom bed increases the overall benzene purity of the system. The amount of catalyst in the system with the higher total metal content and the amount with the lower total metal content can be adjusted to meet the benzene purity needs and to optimize xylene selectivity and ring loss of a particular process setup.

Other systems have shown improvement in xylene selectivity and benzene purity from stacking catalysts with different zeolite compositions. However, none changes the metal concentration while maintaining the same zeolite composition throughout to control the sequence of transalkylation, dealkylation, and cracking reactions.

The transalkylation process is typically a downflow process. There can be two or more catalyst beds. The first bed to be contacted by the feed stream has the highest total metal content of all of the beds. Each successive bed has a lower total metal content than the bed before (i.e., the total metal content of the second bed is less than the first, and the third is less than the second, etc.).

The metal for the first and second bed is selected from Groups 6-10 and 14 of the Periodic Table, or combinations thereof. Suitable metals include, but are not limited to, Mo, Ni, Re, Pt, Pd, or combinations thereof. The metals in the first and second beds (or third bed or more) may be the same or different.

The total metal content of the first catalyst bed is 1 wt % or more, or 2 wt % or more, or 3 wt % or more, or 4 wt % or more, or 5 wt % or more, or 7 wt % or more, or 10 wt % or more, or 12 wt % or more, or 15 wt % or more, or 20 wt % or more, or 25 wt % or more, or 1 wt % to 50 wt %, or 1 wt % to 40 wt %, or 1 wt % to 30 wt %, or 1 wt % to 25 wt %, or 1 wt % to 20 wt %, or 1 wt % to 15 wt %, or 1 wt % to 12 wt %, or 1 wt % to 10 wt %, or 1 wt % to 7 wt %, or 1 wt % to 5 wt %.

The ratio of first catalyst bed to the second catalyst bed is in the range of 1:99 to 75:25, or 1:99 to 70:30, or 1:99 to 65:35, or 1:99 to 60:40, or 1:99 to 55:45, or 1:99 to 50:50, or 5:95 to 75:25, or 5:95 to 70:30, or 5:95 to 65:35, or 5:95 to 60:40, or 5:95 to 55:45, or 5:95 to 50:50, or 10:90 to 75:25, or 10:90 to 70:30, or 10:90 to 65:35, or 10:90 to 60:40, or 10:90 to 55:45, or 10:90 to 50:50.

Any suitable zeolite can be used. Suitable zeolites include, but are not limited to, MFI zeolites, MOR zeolites, MEI zeolites, MFS zeolites, FER zeolites, FAU zeolites, or combinations thereof. Suitable zeolites include, but are not limited to, MFI zeolites, MOR zeolites, or combinations thereof.

The first catalyst bed, the second catalyst bed, or both may optionally contain a binder. Any suitable binder can be used, including but not limited to, an alumina binder. The binder may be present in an amount of 50% wt % or less, or 45 wt % or less, or 40 wt % or less, or 35 wt % or less, or 30 wt % or less, or 25 wt % or less, or 20 wt % or less, or 15 wt % or less, or 10 wt % or less, or 5 wt % or less, or 1 wt % to 50 wt %, or 1 wt % to 45 wt %, or 1 wt % to 40 wt %, or 1 wt % to 35 wt %, or 1 wt % to 30 wt %, or 1 wt % to 25 wt %, or 1 wt % to 20 wt %, or 1 wt % to 15 wt %, or 1 wt % to 10 wt %, or 5 wt % to 50 wt %, or 5 wt % to 45 wt %, or 5 wt % to 40 wt %, or 5 wt % to 35 wt %, or 5 wt % to 30 wt %, or 5 wt % to 25 wt %, or 5 wt % to 20 wt %, or 5 wt % to 15 wt %, or 5 wt % to 10 wt %, or 10 wt % to 50 wt %, or 10 wt % to 45 wt %, or 10 wt % to 40 wt %, or 10 wt % to 35 wt %, or 10 wt % to 30 wt %, or 10 wt % to 25 wt %, or 10 wt % to 20 wt %, or 10 wt % to 15 wt %, or 15 wt % to 50 wt %, or 15 wt % to 45 wt %, or 15 wt % to 40 wt %, or 15 wt % to 35 wt %, or 15 wt % to 30 wt %, or 15 wt % to 25 wt %, or 15 wt % to 20 wt %.

The catalyst described above can be used in a transalkylation process. The transalkylation zone normally operates at conditions including a temperature in the range of 130° C. to 540° C., or 200° C. to 540° C. The transalkylation zone is typically operated at moderately elevated pressures broadly ranging from about 100 kPa to about 10 MPa absolute, or 100 kPa to about 6 MPa absolute. The ratio of hydrogen to hydrocarbon is typically in the range of 1 to 10, or 2 to 5. The transalkylation reaction can be achieved over a wide range of space velocities. That is, volume of charge per volume of catalyst per hour; weight hourly space velocity (WHSV) generally is in the range of from about 0.1 to about 30 $hr^{-1}$. One suitable set of conditions comprises one or more of: a temperature in a range of 200° C. to 540° C., a pressure in a range of 100 kPa to 6 MPa, or a ratio of hydrogen to hydrocarbon of 1 to 10.

The temperature increase across the first bed is utilized in the second bed. Because of its higher metal content, the first bed requires a lower temperature than the second bed with the lower metal content. The exotherm from the first bed is utilized for the second bed.

EXAMPLES

The following examples are presented to only illustrate one possible application of the invention and should not be used to limit the scope of the invention as described in the claims. Many other possible variations may occur within the span of the invention.

Example 1

Transalkylation catalysts comprising two zeolites (the same zeolites in both catalysts), alumina and $MoO_3$ were prepared for comparative pilot plant testing by the forming process called extrusion. Catalyst A and Catalyst B were prepared with 5% Mo and 1% Mo, respectively.

Example 2

The catalyst compositions described in Example 1 were tested in a single bed to evaluate transalkylation in a feed mixture described by Table 1 at about 330-340C, 400 psig, 3 $H_2$/HC, and 3.5 WHSV.

A two bed catalyst system was run as well, where 50% of Catalyst A was stacked on top of 50% of Catalyst B.

TABLE 1

| Feed | Wt % |
|---|---|
| Non Aromatics | 0.1 |
| Benzene | 0.0 |
| Toluene | 50.3 |
| Ethylbenzene | 0.0 |
| Mixed Xylenes | 0.2 |
| Propylbenzene | 1.6 |
| Methylethylbenzene | 9.9 |
| Trimethylbenzene | 30.3 |
| Diethylbenzene + A10 | 1.6 |
| Dimethylethylbenzene | 3.7 |
| Tetramethylbenzene | 1.3 |
| Indane | 0.4 |
| C11+ | 0.5 |

As described in Table 2, Catalyst A with higher metal loading in a single bed has a higher xylene selectivity and methyl group retention, but lower benzene purity than Catalyst B. Stacking Catalyst A over Catalyst B yields the same xylene selectivity as Catalyst A alone, while also improving the benzene purity to an extent that is acceptable by many refiners.

TABLE 2

| | Catalyst A | Catalyst B | 50% Catalyst A (top bed)/ 50% Catalyst B (bottom bed) |
|---|---|---|---|
| A7 + A9 + A10 Conversion (wt %) | 48 | 48 | 48 |
| Reactor Temperature (° C.) | 340 | 331 | 334 |
| Xylene selectivity (wt %) | 72.7 | 73.1 | 73.1 |
| Methyl Retention (mol %) | 98.0 | 98.4 | 98.3 |
| Benzene purity (wt %) | 99.9 | 99.6 | 99.8 |

SPECIFIC EMBODIMENTS

While the following is described in conjunction with specific embodiments, it will be understood that this description is intended to illustrate and not limit the scope of the preceding description and the appended claims.

A first embodiment of the invention is a composition for transalkylation comprising a first catalyst bed comprising a zeolite and a metal selected from Groups 6-10 and 14 of the Periodic Table, or combinations thereof, the first catalyst bed having a total metal content of 1 wt % or more; and a second catalyst bed comprising the zeolite and a second metal selected from Groups 6-10 and 14 of the Periodic Table, or combinations thereof, the total metal content of the first catalyst bed being greater than a total metal content of the second catalyst bed, and wherein the first catalyst bed is positioned to contact a feed before the second catalyst bed. An embodiment of the invention is one, any or all of prior embodiments in this paragraph up through the first embodiment in this paragraph further comprising a third catalyst bed comprising the zeolite and the metal selected from Groups 6-10 and 14 of the Periodic Table, or combinations thereof, the third catalyst bed positioned to contact the feed after the second catalyst bed, the third catalyst bed having a total metal content less than the total metal content of the second catalyst bed. An embodiment of the invention is one, any or all of prior embodiments in this paragraph up through the first embodiment in this paragraph wherein the metal comprises Mo, Ni, Re, Pt, Pd, or combinations thereof. An embodiment of the invention is one, any or all of prior embodiments in this paragraph up through the first embodiment in this paragraph wherein the metal comprises molybdenum. An embodiment of the invention is one, any or all of prior embodiments in this paragraph up through the first embodiment in this paragraph wherein a ratio of the first catalyst bed to the second catalyst bed is in a range of 199 to 7525. An embodiment of the invention is one, any or all of prior embodiments in this paragraph up through the first embodiment in this paragraph wherein a ratio of the first catalyst bed to the second catalyst layer is in a range of 1090 to 5050. An embodiment of the invention is one, any or all of prior embodiments in this paragraph up through the first embodiment in this paragraph wherein the zeolite comprises MFI zeolites, MOR zeolites, MTW zeolites, Type V zeolites, beta zeolite, or combinations thereof. An embodiment of the invention is one, any or all of prior embodiments in this paragraph up through the first embodiment in this paragraph wherein the first catalyst bed or the second catalyst bed or both further comprise a binder. An embodiment of the invention is one, any or all of prior embodiments in this paragraph up through the first embodiment in this paragraph wherein the second catalyst bed has the total metal content less than or equal to 5 wt %.

A second embodiment of the invention is a method of transalkylating a feedstream comprising contacting the feedstream containing one or more of C7+, aromatics to obtain a product stream having an increased concentration of C8 aromatics compared to the feedstream at transalkylation conditions with a catalyst comprising a first catalyst bed comprising a zeolite and a metal selected from Groups 6-10 and 14 of the Periodic Table, or combinations thereof, and optionally a binder, the first catalyst bed having a total metal content of 1 wt % or more; and a second catalyst bed comprising the zeolite and the metal selected from Groups 6-10 and 14 of the Periodic Table, or combinations thereof, and an optional binder, the total metal content of the first catalyst bed being greater than a total metal content of the second catalyst bed, and wherein the first catalyst bed is positioned to contact the feedstream before the second catalyst bed. An embodiment of the invention is one, any or all of prior embodiments in this paragraph up through the second embodiment in this paragraph wherein the metal comprises Mo, Ni, Re, Pt, Pd, or combinations thereof. An embodiment of the invention is one, any or all of prior embodiments in this paragraph up through the second embodiment in this paragraph wherein the metal comprises molybdenum. An embodiment of the invention is one, any or all of prior embodiments in this paragraph up through the second embodiment in this paragraph wherein a ratio of the first catalyst layer to the second catalyst layer is in a range of 199 to 7525. An embodiment of the invention is one, any or all of prior embodiments in this paragraph up through the second embodiment in this paragraph wherein a ratio of the first catalyst bed to the second catalyst layer is in a range of 1090 to 5050. An embodiment of the invention is one, any or all of prior embodiments in this paragraph up through the second embodiment in this paragraph wherein the transalkylation conditions comprise one or more of a temperature in a range of 200° C. to 540° C., a pressure in a range of 100 kPa to 6 MPa, or a ratio of hydrogen to hydrocarbon of 1 to 10. An embodiment of the invention is one, any or all of prior embodiments in this paragraph up through the second embodiment in this paragraph wherein a temperature in the first catalyst bed is lower than a temperature of the second catalyst bed. An embodiment of the invention is one, any or all of prior embodiments in this paragraph up through the second embodiment in this paragraph wherein the catalyst further comprises a third catalyst bed comprising the zeolite, and the metal selected from Groups 6-10 and 14 of the Periodic Table, or combinations thereof, and an optional binder, the third catalyst bed positioned below the second catalyst bed, the third catalyst bed having a total metal content less than the total metal content of the second catalyst bed. An embodiment of the invention is one, any or all of prior embodiments in this paragraph up through the second embodiment in this paragraph wherein the first catalyst bed or the second catalyst bed or both further comprise a binder. An embodiment of the invention is one, any or all of prior embodiments in this paragraph up through the second embodiment in this paragraph wherein the zeolite comprises MFI zeolites, MOR zeolites, MTW zeolites, Type V zeolites, beta zeolite, or combinations thereof.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A catalyst for transalkylation comprising:

a first catalyst bed comprising a zeolite and a metal selected from Groups 6-10 and 14 of the Periodic Table, or combinations thereof, the first catalyst bed having a total metal content of 1 wt % or more; and a second catalyst bed comprising the zeolite and a second metal selected from Groups 6-10 and 14 of the Periodic Table, or combinations thereof, the total metal content of the first catalyst bed being greater than a total metal content of the second catalyst bed, and wherein the first catalyst bed is positioned to contact a feed stream before the second catalyst bed.

2. The catalyst of claim 1 further comprising:

a third catalyst bed comprising the zeolite and a third metal selected from Groups 6-10 and 14 of the Periodic Table, or combinations thereof, the third catalyst bed positioned to contact the feed stream after the second catalyst bed, the third catalyst bed having a total metal content less than the total metal content of the second catalyst bed.

3. The catalyst of claim 1 wherein the metal comprises Mo, Ni, Re, Pt, Pd, or combinations thereof.

4. The catalyst of claim 1 wherein the metal comprises molybdenum.

5. The catalyst of claim 1 wherein a ratio of the first catalyst bed to the second catalyst bed is in a range of 1:99 to 75:25.

6. The catalyst of claim 1 wherein a ratio of weight of the first catalyst bed to weight of the second catalyst bed is in a range of 10:90 to 50:50.

7. The catalyst of claim 1 wherein the zeolite comprises MFI zeolites, MOR zeolites, MT W zeolites, Type V zeolites, beta zeolite, or combinations thereof.

8. The catalyst of claim 1 wherein the first catalyst bed or the second catalyst bed or both further comprise a binder.

9. The catalyst of claim 1 wherein the second catalyst bed has the total metal content less than or equal to 5 wt %.

10. A method of transalkylating a feed stream comprising: contacting the feed stream containing one or more of C7+, aromatics to obtain a product stream having an increased concentration of Cs aromatics compared to the feed stream at transalkylation conditions with a catalyst comprising:

a first catalyst bed comprising a zeolite and a metal selected from Groups 6-10 and 14 of the Periodic Table, or combinations thereof, and optionally a binder, the first catalyst bed having a total metal content of 1 wt % or more; and a second catalyst bed comprising the zeolite and a second metal selected from Groups 6-10 and 14 of the Periodic Table, or combinations thereof, and an optional binder, the total metal content of the first catalyst bed being greater than a total metal content of the second catalyst bed, and wherein the first catalyst bed is positioned to contact the feed stream before the second catalyst bed.

11. The method of claim 10 wherein the metal comprises Mo, Ni, Re, Pt, Pd, or combinations thereof.

12. The method of claim 10 wherein the metal comprises molybdenum.

13. The method of claim 10 wherein a ratio of the first catalyst layer to the second catalyst layer is in a range of 1:99 to 75:25.

14. The method of claim 10 wherein a ratio of the first catalyst bed to the second catalyst layer is in a range of 10:90 to 50:50.

15. The method of claim 10 wherein the transalkylation conditions comprise one or more of: a temperature in a range of 200° C. to 540° C., a pressure in a range of 100 kPa to 6 MPa, or a ratio of hydrogen to hydrocarbon of 1 to 10.

16. The method of claim 10 wherein a temperature in the first catalyst bed is lower than a temperature of the second catalyst bed.

17. The method of claim 10 wherein the catalyst further comprises:

a third catalyst bed comprising the zeolite, and a third metal selected from Groups 6-10 and 14 of the Periodic Table, or combinations thereof, and an optional binder, the third catalyst bed positioned below the second catalyst bed, the third catalyst bed having a total metal content less than the total metal content of the second catalyst bed.

18. The method of claim 10 wherein the first catalyst bed or the second catalyst bed or both further comprise a binder.

19. The method of claim 10 wherein the zeolite comprises MFI zeolites, MOR zeolites, or combinations thereof.

* * * * *